United States Patent [19]

Hermanson

[11] Patent Number: 5,364,985
[45] Date of Patent: Nov. 15, 1994

[54] PROCESS FOR SEPARATING MIXTURE OF ETHYLENE GLYCOL AND DIMETHYL TEREPHTHALATE POLYMERS

[75] Inventor: Paul M. Hermanson, Oak Lawn, Ill.

[73] Assignee: Enviropur Waste Refining and Technology, Inc., The Woodlands, Tex.

[21] Appl. No.: 66,498

[22] Filed: May 24, 1993

[51] Int. Cl.$^5$ .................. C07C 27/26; C07C 29/74
[52] U.S. Cl. ........................... 568/871; 528/490
[58] Field of Search ........................... 568/871

[56] References Cited

U.S. PATENT DOCUMENTS

| | | | |
|---|---|---|---|
| 3,458,583 | 7/1969 | Taul et al. | 568/871 |
| 4,066,835 | 1/1978 | Hahn et al. | 560/98 |
| 4,076,946 | 2/1978 | Millick, III | 560/78 |
| 4,241,216 | 12/1980 | Bergman et al. | 560/99 |
| 4,929,749 | 5/1990 | Gupta et al. | 560/79 |
| 5,051,528 | 9/1991 | Naujokas et al. | 560/78 |

FOREIGN PATENT DOCUMENTS 603142 8/1960 Canada .................. 568/871

OTHER PUBLICATIONS

CA 83(21):178586x, Matsuura et al, BisCibeta.-hydroxyethyl terephthalate and dimethyl terephthalate, 1975.

*Primary Examiner*—Johann Richter
*Assistant Examiner*—Rebecca Cook
*Attorney, Agent, or Firm*—Dressler, Goldsmith, Shore & Milnamow

[57] ABSTRACT

A process for separating ethylene glycol from a mixture of ethylene glycol and dimethyl terephthalate polymers is described. The mixture is comminuted, mixed with water, and agitated at a high fluid shear rate to disperse the polymers. A flocculant and, optionally, a filter aid are added to the mixture. Thereafter, the dimethyl terephthalate polymers are separated from the mixture. The process produces a commercially valuable ethylene glycol stream. The separated dimethyl terephthalate polymers are recovered in a form which facilitates disposal or, alternatively, re-use.

9 Claims, 1 Drawing Sheet

PROCESS FOR SEPARATING MIXTURE OF ETHYLENE GLYCOL AND DIMETHYL TEREPHTHALATE POLYMERS

TECHNICAL FIELD

The invention relates to a method for separating a mixture including ethylene glycol and dimethyl terephthalate polymers. The invention also relates to a method for disposing of an industrial waste by-product stream produced in the course of manufacturing polyethylene terephthalate.

BACKGROUND OF THE INVENTION

Dimethyl terephthalate is widely utilized in the manufacture of polyethylene terephthalate, a plastic employed in plastic beverage containers, Dacron TM clothing material and other commercial products. In the manufacturing process, dimethyl terephthalate typically is mixed with ethylene glycol and brought into contact with an acidic catalyst, such as an oxide of antimony. A substantial portion of the dimethyl terephthalate reacts with the ethylene glycol to produce polyethylene terephthalate, methanol, and water. Some intermediate polymers, such as oligomers of dimethyl terephthalate are also produced.

Polyethylene terephthalate and other relatively volatile components are typically recovered by distillation in a resin tower. As a by-product, the distillation produces a bottoms stream which includes unreacted dimethyl terephthalate, relatively low molecular weight dimethyl terephthalate oligomers, ethylene glycol, and water. Additionally, the bottoms stream often contains a small amount of residual polyethylene terephthalate, traces of the acidic catalyst, and insoluble contaminants. Corrosion products and relatively high molecular weight polymers produced by thermal degradation are examples of such insoluble contaminants.

Previously, unreacted dimethyl terephthalate which entered the bottoms stream has been considered unrecoverable. The bottoms stream is not susceptible to conventional filtration because the mixture of dimethyl terephthalate, ethylene glycol, and water quickly fouls conventional filters. Somewhat longer filter runs can be obtained by applying a filter precoat, such as a coating of diatomaceous earth, on the conventional filters, but such precoats tend to become mixed with the filter cake. Additionally, conventional filtration yields a filter cake of dimethyl terephthalate that is contaminated by catalyst, corrosion products, and thermally degraded polymer products.

Upon leaving the resin tower, the bottoms stream is usually subjected to evaporation, stripping, or distillation steps which reclaim ethylene glycol for recycling and which produce a relatively more concentrated residual bottoms stream. Unfortunately, as the level of ethylene glycol in the residual bottoms stream is reduced, the dimethyl terephthalate and its oligomers become increasingly heat sensitive. Distilling the residual bottoms stream to about 10% to about 15% ethylene glycol content by volume thermally degrades polymers present in the stream to such an extent that the stream exhibits a viscosity similar to modeling clay. For example, the residual bottoms stream is sometimes transported and stored in the form of massive blocks.

Consequently, the residual bottoms stream produced as a by-product of dimethyl terephthalate manufacturing has long been considered worthless. After the residual bottoms stream has been concentrated by removing as much ethylene glycol as is practical, it is commonly incinerated as hazardous waste at significant cost. Alternatively, the residual bottoms stream may be placed in a landfill. Ethylene glycol which remains in the residual bottoms stream is susceptible to leeching and can contaminate groundwater if it escapes the landfill. Regrettably, the residual bottoms stream is a poor candidate for subsequent size reduction processes which might otherwise facilitate disposal or re-use, because the stream is usually a liquid or an extrudable solid which resists pulverizing and grinding.

A need exists for a practical method for separating dimethyl terephthalate polymers from ethylene glycol. Such a recovery process would yield valuable ethylene glycol, and would also prevent unnecessary filling of increasingly scarce landfills.

SUMMARY OF THE INVENTION

The invention is a process for separating dimethyl terephthalate polymers from a mixture that contains ethylene glycol and dimethyl terephthalate polymers. The mixture is rendered pumpable by comminution and water addition, as necessary. The polymers in the pumpable mixture are dispersed by agitation and flocculated. Flocculation permits the dimethyl terephthalate polymers to be separated from the ethylene glycol and water by, for example, filtering or centrifuging. The process produces an aqueous ethylene glycol stream substantially free of the polymers, which can be subsequently concentrated to recover commercially valuable ethylene glycol. The process also can produce a cake of flocculated polymers suitable for subsequent drying and grinding.

In one aspect, the invention is a process for separating ethylene glycol from a mixture which contains ethylene glycol and dimethyl terephthalate polymers. The process comprises providing a pumpable mixture of ethylene glycol, dimethyl terephthalate polymers, and water. For each part by weight of the dimethyl terephthalate polymers, the pumpable mixture contains at least about three parts by weight of water. The mixture is agitated at a fluid shear rate which disperses the dimethyl terephthalate polymers. Subsequently, a flocculant is added to the mixture to flocculate the dimethyl terephthalate polymers. The flocs are separated from the mixture to produce a floc cake suitable for re-use or disposal, and an ethylene glycol stream having a relatively low suspended solids content.

In another aspect, the invention is a process for separating an extrudable mixture that contains dimethyl terephthalate polymers and ethylene glycol. The extrudable mixture is comminuted and mixed with water to produce a pumpable mixture having a weight ratio of the polymers to water in the range of about 1:3 to about 1:9. Thereafter, a flocculant is added to the pumpable mixture in an amount in the range of about 0.01 weight percent to about 2 weight percent, based on the total weight of the pumpable mixture. Flocculated dimethyl terephthalate polymers are separated from the pumpable mixture by filtering through a filter media precoated with a filter aid. The filtrate is an aqueous ethylene glycol stream having a low total suspended solids content. The filtrate is concentrated to produce a product stream rich in ethylene glycol. The floc cake is dried to produce a polymer product.

DETAILED DESCRIPTION OF THE INVENTION

Figure 1:
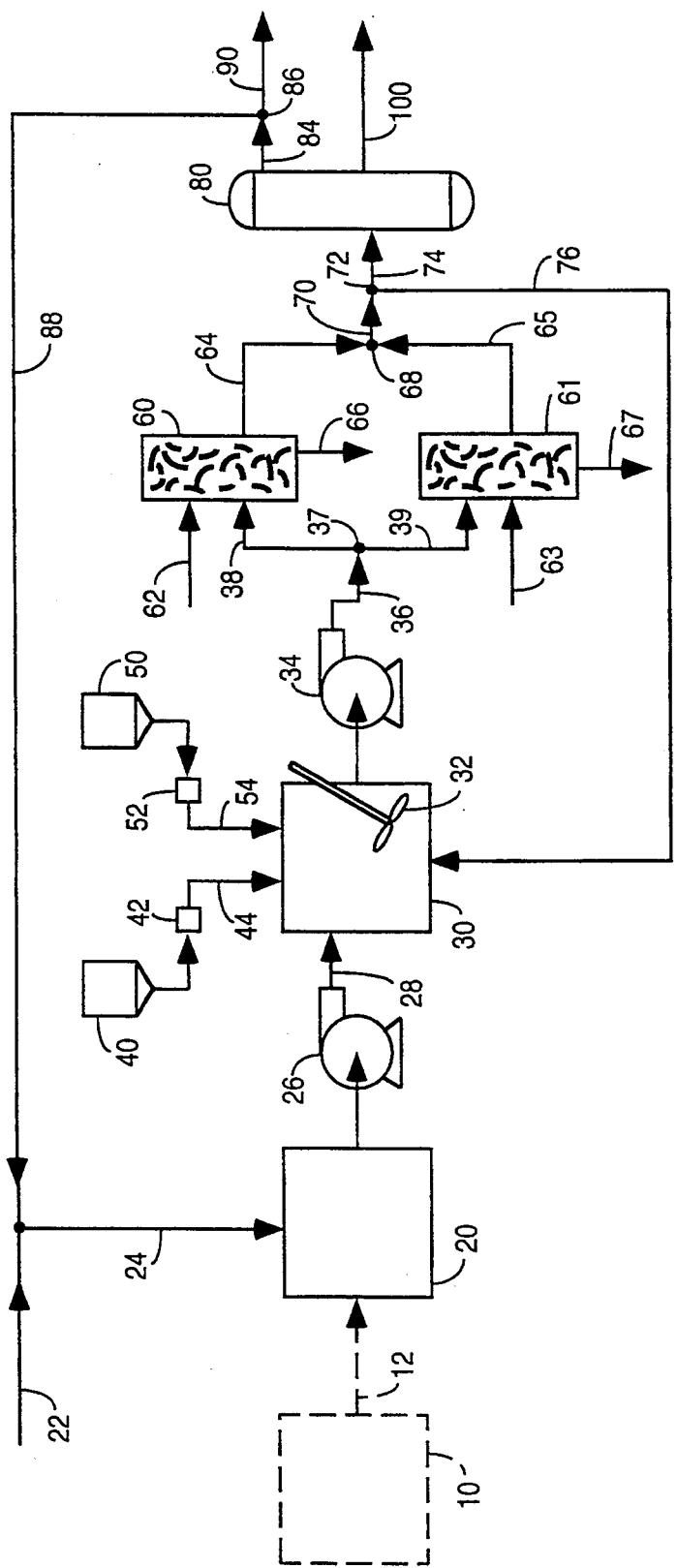
FIG. 1 shows a process flow diagram of a separation process in accordance with the present invention.

The invention can be practiced with any feed stream that contains ethylene glycol and a significant proportion of dimethyl terephthalate polymers. The invention can be practiced with initially dry streams containing dimethyl terephthalate polymers, in which case water is subsequently added. Dimethyl terephthalate polymers have a chain length of at least about 10 terephthalate units, as distinguished from dimethyl terephthalate oligomers which have a chain length of about 8 or less terephthalate units.

Preferably, the feed stream is a by-product produced in the course of manufacturing polyethylene terephthalate (hereinafter referred to as "PET"). For example, the feed stream can be a residual bottoms stream produced by evaporating or distilling a bottoms stream from the resin tower of a PET manufacturing unit. Alternatively, the feed stream may be a bottoms stream which contains a substantial portion of dimethyl terephthalate polymers. The feed stream can be waste material produced in the course of cleaning a PET reactor. In each of these cases, the feed stream may contain oligomers of dimethylene terephthalate, catalysts, and ferrous corrosion products, in addition to the dimethyl terephthalate polymers.

A flow diagram for a process in accordance with the present invention is shown in FIG. 1. A pumpable feed stream is accumulated or, alternatively, prepared in a feed preparation facility 20. Preferably, the feed stream is produced by an upstream PET manufacturing unit 10, which is not part of the present invention. The feed stream may be a liquid or, alternatively, may be an extremely viscous semi-solid that is referred to herein as an extrudable mixture. If the feed stock to be recovered is not received in pumpable form, water or ethylene glycol is added to achieve a pumpable viscosity. Herein, a pumpable viscosity is a viscosity within the practical range of operation for conventional gear pumps. The feed stream may be received in solid blocks of the extrudable mixture, which are cut or extruded to manageable sizes within the preparation facility 20.

Typically, the pumpable mixture received by the feed preparation facility 20 will be acidic and have a pH in the range of about 2 to about 5. In many cases, this relatively acidic pH range is caused by the presence of residual amounts of a catalyst, such as antimony oxide, which is present in the feed stock in trace amounts. A typical feed stock contains antimony oxide in the range of about 1,000 to about 5,000 parts per million by weight.

Before the pumpable mixture leaves the preparation facility 20, a sufficient quantity of water is added via conduit 24, to adjust the weight ratio of dimethyl terephthalate polymers to water in the pumpable mixture to at least about 1:3, preferably to a value in the range of about 1:3 to about 1:9. The water that enters the feed preparation facility 20 via conduit 24 may be fresh make-up water from a conduit 22, recycled water transported by a conduit 88, or a mixture of fresh and recycled water.

The pumpable mixture is delivered by a feed pump 26 through a conduit 28 to a treating tank 30. The treating tank 30 is equipped with an impeller 32 which is capable of rotating or, alternatively, vibrating at high peripheral speeds in order to agitate the pumpable mixture at a relatively high fluid shear rate. Other means for producing high fluid shear rates may be employed in place of the impeller, for example, jet mixers, mixing valves, or sonic mixers.

The agitation is maintained until the dimethyl terephthalate polymers in the pumpable mixture are substantially dispersed. At this time, the pumpable mixture usually takes on a milky appearance. In addition to dispersing the polymers, the agitation produces some reduction in particle size of the polymers.

A flocculant tank 40 contains a flocculant solution which is delivered to the treating tank 30 by a metering pump 42 and a conduit 44. The flocculant solution may contain any flocculant or combination of flocculants that is capable of producing flocs of dimethyl terephthalate polymers from the pumpable mixture. The flocculant can be an inorganic, a synthetic organic, or a naturally occurring organic flocculant. Preferably, the flocculant is an inorganic salt whose effect is primarily electrostatic in nature and does not depend on a specific chemical interaction with suspended particles for effectiveness. Preferably, the flocculant is an inorganic salt selected from the group consisting of ferric chloride, aluminum sulfate, and double sulfate salts of the formula:

$$R_2SO_4 \cdot X_2(SO_4)_3$$

wherein R is an alkali metal or ammonium, and X is a trivalent metal. One example of a suitable double sulfate salt is aluminum potassium sulfate. More preferably, the flocculant is aluminum sulfate.

In place of, or in addition to, the inorganic salt described above, the flocculant solution preferably contains a polymeric flocculant. The polymeric flocculant can be a cationic polymer, such as poly(ethyleneamine), poly(2-hydroxypropyl-1-N-methylammonium chloride), poly(2-hydroxypropyl-1,1-N-dimethylammonium chloride), poly[N-(dimethylaminomethyl)-acrylamide], poly(2-vinylimidazolinum bisulfate), poly(diallyldimethylammonium chloride), poly(N,N-dimethylaminoethyl methacrylate), or poly[N-(dimethylaminopropyl)-methacrylamide].

Alternatively, the polymeric flocculant can be a nonionic polymer such as polyacrylamide, poly(ethylene oxide), or poly(vinylpyrrolidinone).

It is especially preferred that the polymeric flocculant be an anionic polymer such as poly(sodium acrylate), poly(ammonium acrylate), poly(methacrylic acid), or poly(sodium styrene sulfonate). For example, the cationic polymer is preferably a poly(methacrylic acid) polymer which is commercially available under the trade name of Primafloc A-10 from Chemical Dynamics Corporation of South Plainfield, N.J. More preferably the cationic polymer is Dearborn® 407, which is commercially available from Grace Dearborn of Lake Zurich, Ill.

Via the metering pump 42, the flocculant is added to the pumpable mixture in an amount effective to produce visually detectable flocs. The flocculant is preferably added in an amount in the range of about 0.01 weight percent to about 2 weight percent, based on the total weight of the pumpable mixture. Generally, a relatively higher degree of flocculation in the treating tank 30 produces more efficient separation of the polymers in a downstream step of the present process, which will be described below. The level of flocculant addition can be optimized by varying the amount of flocculant added and, simultaneously, observing the efficiency of the downstream separation.

The pumpable mixture and the added flocculant solution are thoroughly mixed within the treating tank 30. Thereafter, a slurry containing a filter aid is desirably metered from a filter aid tank 50 through a metering pump 52 and a conduit 54 into the pumpable mixture. The pumpable mixture is circulated in the treating tank 30 to distribute the filter aid throughout the pumpable mixture.

The pumpable mixture is eventually withdrawn from the treating tank 30 by a transfer pump 34 and delivered to separation means, such as plate filters 60 and 61. The separating means can be a pressure filter such as a drum filter or a disc filter. The separating means can be a continuous precoat pressure filter. Vacuum filters are similarly contemplated for use as the separating means. Alternatively, the separating means may be a centrifuge or a cyclone separator.

Preferably, the separating means, such as the plate filters 61 and 62, include filter media upon which a precoat including a filter aid has been applied. In general, the filter aid as precoat can be used in conjunction with, or as a substitute for, adding filter aid to the treating tank 30. Suitable filter aids include diatomaceous earth, perlite, Fuller's earth, and cellulose fibers. The function of the filter aid is partly, but not exclusively, to increase filtering efficiency, in order to produce filtrates having relatively less total suspended solids content and to promote longer filter run lengths.

It is contemplated that the present process can optionally be employed with filter media, such as septums having relatively small pores, which operate at acceptably high filtering efficiency without filter aids. In that case, the filter aid can be introduced solely through the filter aid tank 50 to aid flocculation or, alternatively, can be dispensed with entirely. The type and amount of pre-coated filter aid is optimized by making engineering adjustments based on observations of the filter in operation for a period of time.

Referring again to FIG. 1, the transfer pump 34 sends the pumpable mixture through the conduit 36 to a branch point 37 in fluid communication with conduits 38 and 39. It is desirable to employ at least two separating means, such as the plate filters 60 and 61, so that one of the plate filters can be cleaned while another remains in service. When the plate filter 60 is taken out of service, a gas such as dry air is introduced through a conduit 62 to displace liquid from the filter and to assist in detaching a floc cake from the filter media. The detached floc cake constitutes a floc product 66, which is composed substantially of dimethyl terephthalate polymers. The floc product 66 normally has the appearance of a fluffy powder. Similarly, gas can be routed through a conduit 63 to the plate filter 61 in order to displace liquid and detach a floc cake producing a floc product 67. Naturally, the floc products 66 and 67 are essentially identical.

The floc products 66 and 67 are easily dried and are well-suited for further processing. Only a very small amount of ethylene glycol remains with the floc products 66 and 67, and even this small amount of ethylene glycol can be further reduced by additional water washing. With or without additional washing, it is contemplated that the floc products 66 and 67 can be used as an environmentally safe filler material, for example, as an extender in road asphalt. Alternatively, the floc products 66 and 67 may be reused as a charge stock for the production of relatively low-grade plastics.

Each of the plate filters 60 and 61 produces an aqueous ethylene glycol filtrate stream which passes through a conduit 64 or 65 to a branch point 68 which is in fluid communication with a conduit 70. One portion of filtrate exits the conduit 70 via a branch point 72 to a conduit 76 which provides for recycling the portion of the filtrate back to the treating tank 30. Another portion of the filtrate simultaneously travels by a conduit 74 to concentrating means, such as a distillation tower 80, where water is removed from the filtrate stream. Water leaves the distillation tower 80 by a conduit 84 which terminates in a branch point 86. The water can either be recycled to the feed preparation facility 20 through the conduit 88 or, alternatively, recovered as a net water product 90.

An ethylene glycol product stream 100 is withdrawn from the bottom of the distillation tower 80. The ethylene glycol product stream 100 is rich in ethylene glycol and has a relatively low total solids content. The ethylene glycol so recovered is commercially valuable and can be reused in plastic manufacturing process, in antifreeze, and for other uses.

The following example is provided to further communicate the invention. The example does not limit the scope of the invention in any way.

EXAMPLE 1

A procedure was performed, in accordance with the present invention, in which residual ethylene glycol was separated from a distillation tower bottoms sample containing ethylene glycol, diethylene glycol, dimethyl terephthalate polymers, and various contaminants. In the procedure, approximately five gallons of an aqueous mixture including 20 percent by weight of the distillation tower bottoms sample was prepared. A standard household blender was utilized to disperse the sample in several relatively small batches of water. To each batch, 0.01 weight percent of aluminum sulfate and 0.01 weight percent of an anionic polymer flocculant were added. The anionic polymer flocculant was Dearborn ® 407, commercially available from Grace Dearborn of Lake Zurich, Ill. Each batch was subjected to additional blending, 0.1 weight percent of Fuller's earth was added, and the batches were blended again. All of the batches were subsequently combined in a feed tank.

A gear pump transported the mixture from the feed tank to a filter press. The press was equipped with filters having a nominal pore size of 25 microns. The press was capable of holding a filter cake with a maximum volume of about 90 cubic inches.

The gear pump continued to draw suction from the feed tank for a period of about 45 minutes during which approximately 3 gallons of the mixture were pumped to the filter. At that time, slurry flow was terminated and compressed air was passed through the filter press to substantially displace liquid from the filter press. Air flow was continued for about 15 minutes, then the press was opened and inspected.

Inspection revealed that substantially all of the volume available in the filter press for forming a filter cake was filled with a beige powdery material. The filtrate was transparent and exhibited a yellowish color. The glycol content of the filtrate was determined analytically to be about 10 percent by weight. The results of this procedure indicate that a distillation tower bottoms stream can be separated into a powdery solid filter cake and a glycol-containing filtrate by the method of the present invention.

The invention is communicated herein by description, hypotheses, examples, and figures. The description, examples, and figures do not limit the scope of the invention or the scope of the appended claims. The specification will undoubtedly suggest other, similar aspects of the invention to those skilled in the art. However, such aspects are within the scope of the invention. Similarly, the success of the invention does not depend on the correctness of the hypotheses, which are presented only to better communicate the invention.

What is claimed is:

1. A process for separating ethylene glycol from a mixture that contains ethylene glycol and dimethyl terephthalate polymers, which comprises:

providing a pumpable mixture that contains ethylene glycol, dimethyl terephthalate polymers, and at least about three parts by weight of water per part of dimethyl terephthalate polymers;

agitating said mixture at a fluid shear rate effective to disperse the dimethyl terephthalate polymers in the ethylene glycol and the water;

adding a flocculant to said mixture in an amount in the range of about 0.01 weight percent to about 2 weight percent based on the total weight of the pumpable mixture, the flocculant containing an inorganic salt selected from the group consisting of aluminum sulfate and double sulfate salts of the formula:

$$R_2SO_4 \cdot X_2(SO_4)_3$$

where R is an alkali metal or ammonium, and X is a trivalent metal to flocculate substantially all the dimethyl terephthalate polymers; and separating the flocculated dimethyl terephthalate polymers from said mixture to produce an aqueous ethylene glycol stream.

2. The process of claim 1 wherein said providing of the pumpable mixture further comprises comminuting an extrudable mixture of dimethyl terephthalate polymers and ethylene glycol and adding water to the extrudable mixture.

3. The process of claim 1 wherein said pumpable mixture contains one part by weight of dimethyl terephthalate polymers and in the range of about three to about nine parts by weight of water.

4. The process of claim 1 wherein said inorganic salt is aluminum sulfate.

5. The process of claim 1 wherein said flocculant also contains an anionic polymer.

6. The process of claim 1 wherein said separating of said flocculated dimethyl terephthalate polymers from said pumpable mixture further comprises filtering the pumpable mixture through filter media in the presence of a filter aid selected from the group consisting of diatomaceous earth, perlite, Fuller's earth, and cellulose fibers.

7. The method of claim 1 which further comprises concentrating said aqueous ethylene glycol stream to produce a product stream rich in ethylene glycol.

8. The method of claim 1 wherein said separating of said flocculated polymers produces a floc cake which is dried and comminuted to produce a particulate product.

9. A process for separating an extrudable mixture that contains ethylene glycol and dimethyl terephthalate polymers, which comprises:

comminuting an extrudable mixture containing dimethyl terephthalate polymers and ethylene glycol and adding water to produce a pumpable mixture containing ethylene glycol, dimethyl terephthalate polymers, and water, having a weight ratio of dimethyl terephthalate polymers to water in the range of about 1:3 to about 1:9;

agitating said pumpable mixture to disperse said dimethyl terephthalate polymers;

adding to said pumpable mixture an amount of inorganic salt flocculant in the range of about 0.01 weight percent to about 2 weight percent, based on the total weight of the pumpable mixture flocculent containing an inorganic salt selected from the group consisting of aluminum sulfate and double sulfate salts of the formula:

$$R_2SO_4 \cdot X_2(SO_4)_3$$

where R is an alkali metal or ammonium, and X is a trivalent metal;

separating flocculated dimethyl terephthalate polymers from said pumpable mixture by filtering through a filter media precoated with a filter aid to produce a floc cake and an aqueous ethylene glycol stream;

drying said floc cake to produce a polymer product; and concentrating said aqueous ethylene glycol stream to produce a product stream rich in ethylene glycol.

* * * * *